United States Patent [19]
Wood et al.

[11] 3,963,795
[45] June 15, 1976

[54] SEPARATION OF ISOMERS BY SELECTIVE MELTING IN AN IMMISCIBLE LIQUID

[75] Inventors: George R. Wood, Winfield; Chang-Man Park, Naperville, both of Ill.

[73] Assignee: Standard Oil Company, Chicago, Ill.

[22] Filed: Dec. 20, 1974

[21] Appl. No.: 535,032

[52] U.S. Cl. .............................. 260/674 A; 23/296; 62/58; 260/674 N; 260/674 R
[51] Int. Cl.$^2$ .......................................... C07C 7/14
[58] Field of Search ........ 260/674 A, 674 N, 674 R; 62/58 R, 58 XY; 23/296

[56] References Cited
UNITED STATES PATENTS

| | | | |
|---|---|---|---|
| 2,296,459 | 9/1942 | Schutte | 260/674 |
| 2,398,526 | 4/1946 | Greenberg | 260/674 |
| 2,540,977 | 2/1951 | Arnold | 260/674 |
| 3,173,960 | 3/1965 | Robinson | 260/674 |
| 3,544,646 | 12/1970 | Broughton et al. | 260/674 |
| 3,643,453 | 2/1972 | Groothuis et al. | 260/674 |
| 3,758,601 | 9/1973 | Wylie | 260/674 |

Primary Examiner—Delbert E. Gantz
Assistant Examiner—C. E. Spresser
Attorney, Agent, or Firm—James L. Wilson; Arthur G. Gilkes; William T. McClain

[57] ABSTRACT

A process is disclosed for separating the isomers of xylene from a mixture of $C_8$ aromatic isomers by the steps of:

1. cooling the $C_8$ aromatic isomers to a temperature of about −65°C to about −90°C to form a slurry of xylene isomer crystals,
2. separating the crystals from the crystallization mother-liquor and washing the xylene isomer crystals with an immiscible liquid,
3. forming a slurry of the washed xylene crystals with the immiscible liquid,
4. warming the slurry to a temperature of about −50°C to about −25°C whereby meta-xylene crystals are melted selectively and the melt is drawn off,
5. further warming the slurry to a temperature of about −25°C to about 13°C whereby ortho-xylene crystals are melted selectively and the melt is drawn off, and
6. separating the remaining para-xylene from the immiscible liquid.

For effective separation of the xylene isomers, the immiscible liquid has a freezing point below about −75°C and a specific gravity at −50°C between about 0.90 and 1.05. A suitable liquid comprises water, methanol and ethylene glycol mixture.

9 Claims, 1 Drawing Figure

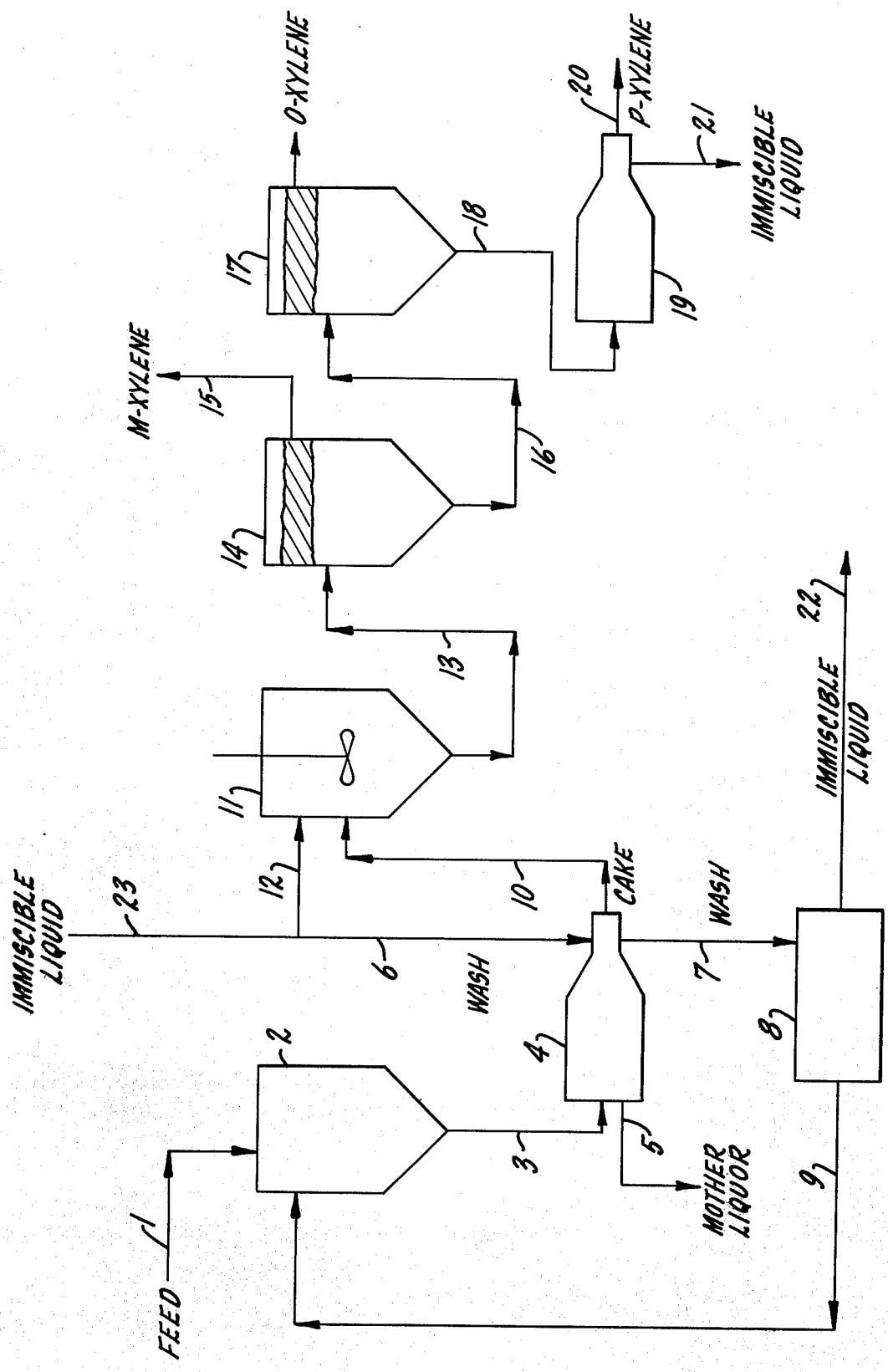

SEPARATION OF ISOMERS BY SELECTIVE MELTING IN AN IMMISCIBLE LIQUID

BACKGROUND OF THE INVENTION

This invention relates to the separation of individual isomers from a mixture of isomers by a process of selectively melting the isomers in the presence of an immiscible liquid. More particularly this invention relates to the separation of para-, meta-, and ortho-xylenes by a process of selectively melting the isomers in the presence of an immiscible liquid comprising a water, a lower alkanol, and a lower glycol mixture.

In recent years there has been a growing need for feedstocks rich in each of the isomers of xylene. Feedstocks rich in para-xylene, for example, are needed for the production of the terephthalic acid; those rich in meta-xylene, for the production of isophthalic acid; and those rich in ortho-xylene, for the production of phthalic anhydride. These products are important commercially and are used for the production of polyester fibers, alkyd resins, protective coatings, and the like.

The separation of xylene isomers by fractional distillation is extremely difficult because of the small differences in their boiling points as shown in the following table:

|  | m.p. | b.p./760mm |
|---|---|---|
| Ethylbenzene | −95°C | 136°C |
| Para-xylene | 13.3 | 138.3 |
| Meta-xylene | −47.9 | 139.1 |
| Ortho-xylene | −25.2 | 144.4 |

On the other hand, the differences in melting points are relatively large and, as a consequence, several processes have been developed utilizing fractional crystallization. In particular, crystallization processes for the separation of para-xylene are well known and are practiced on a large commercial scale. One of the serious drawbacks of such processes is that the amount of para-xylene that can be recovered is limited by the crystallization threshold of the other xylene isomers; that is, eutectic solutions are formed which upon further cooling yield solids of more than one isomer. Not only does this property limit recovery of one isomer but it also prevents the separation of a second isomer in its pure form. The state of the art is further illustrated by U.S. Pat. No. 3,798,282 which discloses the separation of high-purity metaxylene from a mixture of meta and para crystals by crystal size classification. U.S. Pat. No. 2,769,852 is directed primarily to the separation of para-xylene by crystallization of a xylene concentrate in methanol-water mixtures. U.S. Pat. No. 3,758,601 is also primarily concerned with the separation of para-xylene from a hydrocarbon mixture by crystallization in a water-methanol-glycol mixture. Examples of other patents teaching fractional crystallization techniques are U.S. Pat. No. 2,724,007; U.S. Pat. No. 3,643,453; and U.S. Pat. No. 3,825,614. All of these patents utilize crystallization as a technique for isolating a single isomer, specifically either para-xylene or meta-xylene. None of these patents discloses or suggests a process of selective melting in the presence of an immiscible liquid for separation of all three xylene isomers.

SUMMARY OF THE INVENTION

It has now been found, in accordance with this invention, that when a mixture of $C_8$ aromatic isomers is crystallized at a temperature in the range of about −65° to −90°C a mixture of discrete para-, meta-, and ortho-xylene crystals is obtained. For the purposes of this invention it is important that the isomers be obtained in the form of substantially discrete crystals; that is it is important that occlusion of one isomer in the crystal of another isomer and the formation of solid solutions be minimized. The mixture of crystalline xylene isomers is separated from its mother liquor, suitably by centrifugation, and is washed free of adhering mother liquor with an immiscible liquid. A slurry is formed of the immiscible liquid and the washed xylene crystals, the immiscible liquid serving as a barrier between individual crystals which allows each crystal to behave as an isolated thermodynamic system. And, because each crystal is a substantially pure isomeric solid, it will melt only when the temperature is raised to its melting point. Thus, when the slurry of xylene crystals and immiscible liquid is warmed to a temperature of about −50° to about −25°C, meta-xylene crystals melt selectively to form an organic layer of density lower than the immiscible liquid which layer can be drawn off. Further warming of the slurry to a temperature of about −25°C to about 13°C melts the ortho-xylene crystals which can be similarly drawn off, and the para-xylene crystals are left behind. The para-xylene crystals can be readily separated by decantation, filtration, centrifugation, melting, separating as a liquid, or by other suitable means.

The immiscible liquid suitable for use in the process of this invention has the following properties: (1) a freezing point below about −75°C, (2) miscibility with xylene isomers of less than about 0.1 percent by weight, (3) a specific gravity that lies between that of solid and liquid xylenes, suitably a specific gravity at −50°C of from about 0.90 to about 1.05, and (4) a low viscosity, for example less than about 5,000 centipoises at −80°C. It is also desirable that the liquid be low in cost and non-corrosive. Liquids having these properties are obtained by blending water, a $C_1$ to $C_4$ alkanol, and a glycol, particularly ethylene glycol, propylene glycol, or butylene glycol. Suitable liquids contain about 45–70 weight percent of the alkanol, 5–40 weight percent of the glycol, with the balance being water. particularly useful compositions contain methanol, ethylene glycol, and water in ratios by weight of 60:15:25; 55:15:30; and 50:35:15.

The invention will be further described by reference to the drawing which is a flow diagram of a process for separating the isomers of xylene by selectively melting the isomers in the presence of an immiscible liquid.

SPECIFIC EMBODIMENTS OF THE INVENTION

Mixtures of $C_8$ aromatic isomers that can be used in the present invention include, for example, $C_8$ aromatic streams from petroleum reforming or from xylene isomerizing process; reject filtrate from para-xylene crystallization plants; products of toluene disproportionation; and products of the transalkylation of toluene and $C_9$ aromatics. The distribution of isomers in such mixtures will range as follows: 0–20 weight percent ethylbenzene; 8–24 weight percent para-xylene; 8–24 weight percent meta-xylene; and 20–26 weight percent ortho-xylene. Present also may be up to about 15 weight percent of hydrocarbons such as $C_8$ naphthenes, toluene, $C_9$ aromatics, and $C_1 - C_{10}$ paraffins. Typical distributions of $C_8$ aromatic isomers in specific mixtures are shown in the following table; all numbers are expressed as weight percentages.

| | Reject Filtrate | Extracted Petroleum Reformate | Unextracted Petroleum Reformate | Xylene Isomerizate |
|---|---|---|---|---|
| $C_8$ Naphthene | 1.4 | 0.1 | — | 1.7 |
| Toluene | 0.3 | 0.2 | 1 | 0.3 |
| Ethylbenzene | 16.0 | 16.4 | 15.0 | 14.2 |
| Para-xylene | 9.0 | 19.0 | 16.7 | 18.5 |
| Meta-xylene | 50.0 | 43.1 | 37.8 | 43.9 |
| Ortho-xylene | 23.0 | 19.9 | 18.5 | 20.8 |
| $C_9$ Aromatics | 0.3 | 1.3 | 1.0 | 0.6 |
| $C_9$ Paraffins | — | — | 10.0 | — |

To demonstrate the principle of isomer separation in an immiscible liquid, three experiments were conducted in laboratory scale equipment. Slurries of meta- and para-xylene solids in an immiscible liquid were prepared and warmed to a temperature that was between the melting points of pure meta- and pure para-xylene by adding the cold slurry to a large amount of warm immiscible liquid. In each experiment this warming resulted in the melting of a portion of the solids and in the formation of a liquid layer atop the immiscible liquid, while the remaining solids settled to the bottom of the vessel. The experimental conditions, recoveries, and compositions are presented in the following table.

1 to crystallizer vessel 2 where it is cooled to $-81.5°C$ to form a slurry of crystals of xylene isomers. The slurry is pumped through line 3 to centrifuge 4 where 64 pounds of mixed xylene crystals is obtained and 36 pounds of mother liquor is drawn off through line 5. The mother liquor has the composition: 45 weight percent ethylbenzene, 36 weight percent meta-xylene, 15 weight percent ortho-xylene and 4 weight percent para-xylene. The solid crystals in centrifuge 4 are washed with an immiscible liquid introduced through line 6 at a temperature of $-70°C$. The immiscible liquid is a blend of 35 percent water and 65 percent methanol. The wash liquid passes through line 7 to liquid-liquid separator 8 where a small amount of mother liquor is separated and recycled through line 9 to crystallizer 2. The washed cake containing xylene isomers is transferred through line 10 to a slurry drum 11 whre it is slurried at $-70°C$ with 600 pounds of immiscible liquid (35 weight percent water, 65 weight percent methanol) introduced through line 12. The slurry is transferred through line 13 to selective melting drum 14 where it is heated to $-35°C$. About 32.3 pounds of liquid meta-xylene is formed, separates from the slurry, and is drawn off through line 15. The remaining slurry is pumped through line 16 to selective melting drum 17 where it is heated to $-15°C$. About 14.6 pounds of liquid ortho-xylene is formed, separates from the slurry, and is drawn off through line 24. The remaining slurry is transferred through line 18 to centrifuge 19 where 17.5 pounds of para-xylene is recovered and removed through line 20. Immiscible liquid obtained at

SUMMARY OF EXPERIMENTS

| Example | I | II | III |
|---|---|---|---|
| Immiscible Liquid | 60% Methanol<br>40% $H_2O$ | 65% Methanol<br>35% $H_2O$ | 50% Methanol<br>35% Ethylene glycol<br>15% $H_2O$<br>0.1% Surfactant* |
| Slurry: | | | |
| Meta-xylene | 6 ml (.375) | 10 ml (.50) | 12 ml (.444) |
| Para-xylene | 10 ml (.625) | 10 ml (.50) | 15 ml (.556) |
| Immiscible Liquid | 100 ml | 200 ml | 270 ml |
| Temperature, °C | −60 | −56 | −60 |
| Warming Immiscible Liquid | 500 ml at 0°C | 600 ml at 0°C | 200 ml at 0°C |
| Recovery & Composition: | | | |
| Liquid Phase | — | 11 ml | 10 ml |
| Wt. % Meta-xylene | 78.5 | 65.0 | 57.7 |
| Para-xylene | 21.5 | 35.0 | 42.1 |
| Solid Phase | — | 3.5 ml | 3 ml |
| Wt. % Meta-xylene | 3.4 | 27.2 | 21.5 |
| Para-xylene | 96.5 | 72.8 | 78.5 |

*Polyoxyethylene sorbitan monopalmitate

As is evident from the preceding table, meta-xylene is enriched in the liquid phase and para-xylene is enriched in the solid phase, clearly demonstrating the efficacy of the invention. It should be pointed out that the separation efficiency observed from the three experiments is short of the theoretically perfect separation. However, this is primarily due to a great deal of coagulation and aggregation which took place between xylene liquid and crystals. In plant-scale equipment, proper design of slurry drums and liquid-solid separators can minimize such coagulation and aggregation.

Operation of the process of this invention on a larger scale is described with reference to the drawing. One hundred pounds of typical petroleum reformate stream containing 16 weight percent ethylbenzene, 19 weight percent para-xylene, 45 weight percent meta-xylene, and 20 weight percent ortho-xylene is fed through line lines 21 and 22 is recycled to the process via line 23.

It is contemplated that the process of this invention can be advantageously applied to the separation of a single isomer from a mixture of isomers as well as the separation of all the isomers. Thus, for example, in the preceding example described with reference to the drawing if only meta-xylene is the desired isomer the process is terminated after meta-xylene is withdrawn from selective melting drum 14 through line 15. If only ortho-xylene is the desired isomer, the process is terminated after ortho-xylene is withdrawn from selective melting drum 17 through line 24. If only para-xylene is the desired isomer, meta-xylene and ortho-xylene are melted together in either selective melting drum 14 or 17, the molten mixture of isomers is withdrawn through line 15 or 24, and the para-xylene crystals are recovered at line 20 after centrifugation in centrifuge 19.

Although the process of this invention has been described by reference to separation of xylene isomers, it can be advantageously applied to the separation of other isomers, particularly those that are closeboiling and difficult to separate by conventional fractionation processes. Examples of other isomer mixtures that can be used to advantage are mixtures of $C_9$ aromatic hydrocarbons such as hemimellitene, pseudocumene, and 1-methyl-4-ethylbenzene; mixtures of $C_{10}$ aromatic hydrocarbons such as prehnitene, isodurene and durene; mixtures of $C_{11}$ aromatic hydrocarbons such as α-methylnaphthalene and β-methylnaphthalene; and mixtures of $C_{12}$ aromatic hydrocarbons such as isomers of dimethylnaphthalene, particularly mixtures containing 2,6-dimethylnaphthalene and 2,7-dimethylnaphthalene. In general, separation of isomers in mixtures of $C_8$–$C_{12}$ alkyl-substituted aromatic hydrocarbons can be effected in the process of this invention.

Although the present invention has been described with reference to certain specific preferred embodiments thereof, the invention is not limited thereto, but includes within its scope such modifications and variations as come within the scope and spirit of the appended claim.

We claim:
1. A process for separating at least one isomer from a mixture of isomers, said isomers having distinct melting points, which process comprises the steps of:
   a. cooling said mixture of isomers to a temperature below the crystallization temperature of the isomer to be separated to obtain crystals of discrete isomers in mother liquor;
   b. separating said crystals from said mother liquor;
   c. displacing adhering mother liquor from said crystals and admixing said crystals with an immiscible liquid cooled to a temperature below the melting point of the isomer to be separated and having a specific gravity that is higher than the specific gravity of the liquid phase of the isomer to be separated but lower than the specific gravity of the crystalline phase of said isomers;
   d. heating the mixture of step (c) to at least the melting point of said isomer to be separated to selectively melt said isomer to be separated and form said liquid phase of said isomer to be separated, said liquid phase of said isomer to be separated being distinct from both the immiscible liquid and the remaining of said crystals; and
   e. separating said liquid phase of said isomer to be separated from the product of step (d).

2. The process of claim 1 wherein the mixture of isomers comprises alkyl-substituted aromatic hydrocarbons containing from 8 to 12 carbon atoms.

3. The process of claim 1 wherein the mixture of isomers comprises meta-xylene, ortho-xylene, and para-xylene.

4. The process of claim 1 wherein the mixture of isomers comprises isomers of dimethylnaphthalene.

5. A process for separating isomers from a mixture of isomers, said isomers having distinct melting points, which process comprises the steps of:
   a. cooling said mixture of isomers to a temperature below the crystallization temperatures of the isomers to be separated to obtain crystals of discrete isomers in mother liquor;
   b. separating said crystals from said mother liquor;
   c. displacing adhering mother liquor from said crystals and admixing said crystals with an immiscible liquid cooled to a temperature below the melting point of the isomer last to crystallize and having a specific gravity that is higher than the specific gravities of the liquid phases of the isomers to be separated but lower than the specific gravity of the crystalline phase of said isomers;
   d. heating the mixture of step (c) to at least the melting point of the isomer first to melt to selectively melt said isomer first to melt and form a liquid phase of said isomer first to melt, said liquid phase of said isomer first to melt being distinct from both the immiscible liquid and the remaining of said crystals;
   e. separating said liquid phase of said isomer first to melt from the product of step (d);
   f. repeating steps (d) and (e) until the last admixture is of the highest melting isomer in the immiscible liquid; and
   g. separating the highest melting isomer from the immiscible liquid.

6. The process of claim 5 wherein the mixture of isomers comprises metaxylene, ortho-xylene, and para-xylene.

7. The process of claim 6 wherein the immiscible liquid comprises water, a $C_1$ to $C_4$ alkanol, and a glycol selected from the group consisting of ethylene glycol, propylene glycol, and butylene glycol.

8. A process for separating individual xylene isomers from a mixture of $C_8$ aromatic hydrocarbons comprising the steps of:
   a. cooling said $C_8$ aromatic hydrocarbon mixture to a temperature in the range from about −65° to about −90°C to obtain crystals of discrete xylene isomers in mother liquor;
   b. separating said crystals of xylene isomers from said mother liquor;
   c. displacing adhering mother liquor from said crystals of xylene isomers and admixing them with an immiscible liquid at a temperature in the range of from about −50°C to about −90°C, said immiscible liquid comprising a mixture of water and methanol in proportions such that the specific gravity at −50°C is in the range of from about 0.90 and about 1.05 and the freezing point is below about −75°C;
   d. heating the mixture of step (c) to selectively melt metaxylene crystals and form a meta-xylene liquid phase distinct from both the immiscible liquid and the remaining ortho- and para-xylene crystals;
   e. separating the meta-xylene liquid phase from the product of step (d) to form a meta-xylene-free product;
   f. heating the meta-xylene-free product of step (e) to selectively melt ortho-xylene crystals and form an ortho-xylene liquid phase distinct from both the immiscible liquid and the remaining para-xylene crystals;
   g. separating the ortho-xylene liquid phase from the product of step (f) to form an ortho-xylene-free product; and
   h. separating para-xylene from the ortho-xylene-free product of step (g).

9. The process of claim 8 wherein the mixture of $C_8$ aromatic hydrocarbons comprises from about 15 weight percent to about 20 weight percent ethylbenzene, from about 10 weight percent to about 20 weight percent para-xylene, from about 35 weight percent to about 50 weight percent meta-xylene and from about 20 weight percent to about 25 weight percent ortho-xylene.

* * * * *